US011978203B2

(12) United States Patent
Kim et al.

(10) Patent No.: US 11,978,203 B2
(45) Date of Patent: May 7, 2024

(54) DENTAL OBJECT DETECTION METHOD, AND IMAGE MATCHING METHOD AND DEVICE USING DENTAL OBJECT

(71) Applicant: DIO CORPORATION, Busan (KR)

(72) Inventors: Jin Cheol Kim, Busan (KR); Jin Baek Kim, Busan (KR)

(73) Assignee: DIO CORPORATION, Busan (KR)

( * ) Notice: Subject to any disclaimer, the term of this patent is extended or adjusted under 35 U.S.C. 154(b) by 407 days.

(21) Appl. No.: 17/602,677

(22) PCT Filed: Feb. 26, 2020

(86) PCT No.: PCT/KR2020/002756
§ 371 (c)(1),
(2) Date: Oct. 8, 2021

(87) PCT Pub. No.: WO2020/209496
PCT Pub. Date: Oct. 15, 2020

(65) Prior Publication Data
US 2022/0164954 A1 May 26, 2022

(30) Foreign Application Priority Data

Apr. 11, 2019 (KR) .................. 10-2019-0042382
Apr. 11, 2019 (KR) .................. 10-2019-0042383

(51) Int. Cl.
*G06T 7/30* (2017.01)
*A61B 6/03* (2006.01)
(Continued)

(52) U.S. Cl.
CPC ............ *G06T 7/0012* (2013.01); *A61B 6/032* (2013.01); *A61B 6/51* (2024.01); *A61C 9/0053* (2013.01);
(Continued)

(58) Field of Classification Search
CPC .......... G06T 7/0012; G06T 7/30; G06T 7/60; G06T 7/70; G06T 2207/10081;
(Continued)

(56) References Cited

U.S. PATENT DOCUMENTS

2006/0083422 A1 4/2006 Ernst et al.
2017/0169562 A1 6/2017 Somasundaram et al.
(Continued)

FOREIGN PATENT DOCUMENTS

JP 2010000349 1/2010
JP 2018120283 8/2018
(Continued)

OTHER PUBLICATIONS

Olivier de Waard et al., "A novel method for fusion of intra-oral scans and cone-beam computed tomography scans for orthognathic surgery planning"; 2016; Journal of Cranio-Maxillo-Facial Surgery; pp. 160-166. (Year: 2016).*
(Continued)

*Primary Examiner* — Siamak Harandi
(74) *Attorney, Agent, or Firm* — K&L Gates LLP (57) ABSTRACT

An image registration method using a dental object, comprises a generation step of generating a plurality of reference points spaced apart from each other in an oral scan image of a registration target and a computed tomography (CT) image of a registration target, respectively; and a step of registering the oral scan image of the registration target and the CT image of the registration target by using the reference point of the oral scan image (a first reference point) and the reference point of the CT image (a second reference point), wherein the first and second reference points comprise a reference point for one frontmost tooth in the front teeth area and a reference point for two teeth on both rearmost sides of the back teeth area, and wherein the first reference point is
(Continued)

derived from an object which is a simplified shape of the teeth.

8 Claims, 9 Drawing Sheets

(51) Int. Cl.
    *A61B 6/51*     (2024.01)
    *A61C 9/00*     (2006.01)
    *G06T 7/00*     (2017.01)
    *G06T 7/60*     (2017.01)
    *G06T 7/70*     (2017.01)
    *G06V 10/25*     (2022.01)
    *G06V 20/50*     (2022.01)

(52) U.S. Cl.
    CPC .................. *G06T 7/30* (2017.01); *G06T 7/60* (2013.01); *G06T 7/70* (2017.01); *G06V 10/25* (2022.01); *G06V 20/50* (2022.01); *G06T 2207/10081* (2013.01); *G06T 2207/20081* (2013.01); *G06T 2207/30036* (2013.01)

(58) Field of Classification Search
    CPC . G06T 2207/20081; G06T 2207/30036; G06T 2207/10028; G06T 2207/20084; G06T 7/33; A61B 6/032; A61B 6/51; A61B 2505/05; A61B 5/0064; A61B 5/0088; A61B 5/4547; A61B 5/743; A61B 5/7485; A61B 5/682; A61B 2576/02; A61C 9/0053; G06V 10/25; G06V 20/50
See application file for complete search history.

(56) References Cited

U.S. PATENT DOCUMENTS

| | | |
|---|---|---|
| 2018/0122089 A1 | 5/2018 | Kim et al. |
| 2018/0168780 A1 | 6/2018 | Kopelman et al. |

FOREIGN PATENT DOCUMENTS

| | | |
|---|---|---|
| KR | 20110138125 | 12/2011 |
| KR | 20140015239 | 2/2014 |
| KR | 20160149301 | 12/2016 |
| KR | 20170126860 | 11/2017 |
| KR | 20170127950 | 11/2017 |
| KR | 101913586 | 11/2018 |
| TW | 201836558 | 10/2018 |

OTHER PUBLICATIONS

Partial Supplementary Search Report issued to related EP Application No. 20787897.6, dated Dec. 6, 2022, 13 pages.

* cited by examiner

DENTAL OBJECT DETECTION METHOD, AND IMAGE MATCHING METHOD AND DEVICE USING DENTAL OBJECT

PRIORITY CLAIM AND CROSS-REFERENCE TO RELATED APPLICATIONS

This application is a 371 application of PCT/KR2020/002756, filed on Feb. 26, 2020, which claims priority to and the benefit of Korean Patent Application Nos. 10-2019-0042382 and 10-2019-0042383, filed on Apr. 11, 2019, the disclosures of which are incorporated herein by reference in their entirety.

BACKGROUND

1. Field of the Invention

The present invention relates to a method for detecting an object of each tooth in an oral scan image, and a method and apparatus capable of performing image registration between an oral scan image and a CT image using an object of each tooth in an oral scan image and a computed tomography (CT) image of the inside of the oral cavity.

2. Discussion of Related Art

In the field of dentistry, various procedures are performed using various images of the inside of the oral cavity. Such images include an oral scan image, a computed tomography (CT) image, and a magnetic resonance image (MRI). Among them, an oral scan image is a three-dimensional image that displays the surface state of a tooth, unlike a CT image and MRI, which are three-dimensional images that display even the internal state of a tooth.

Meanwhile, each tooth needs to be separately detected in the oral scan image for use as a reference point of image registration with a CT image, for identifying an implant placement position, and for identifying a dental arch shape, etc. To this end, conventionally, each tooth is detected using curvature information in an oral scan image. However, in such a conventional detection method, there was a problem in that have a problem in that the detection error occurs frequently because the boundary between the teeth is ambiguous and the curvature information of the tooth and the gum is similar, and the detection time and efficiency are deteriorated because the load according to the detection is large.

Meanwhile, in the field of computer vision, when the same target is photographed from different times, measurement methods, or viewpoints, etc., images having different coordinate systems are obtained, and image registration refers to processing for displaying these different images in one coordinate system.

In particular, in the field of dentistry, image registration is performed between an oral scan image and a CT image before a procedure such as an implant. In this case, the registered image can be used as important data for determining the optimal implant operation position by allowing the location of the bone tissue and neural tube to be identified.

However, in a conventional method for image registration between an oral scan image and a CT image, image registration is performed using a marker of each image manually designated by a user, or image registration is performed by comparing the distance between all vertexes included in each image. As a result, the conventional method has a problem in that not only the speed of image registration is reduced due to a large load, but also the image registration is inaccurate due to inaccurate characteristics of manual markers and vertexes.

SUMMARY OF THE INVENTION

The present invention is directed to providing a method for detecting an object corresponding to each tooth in an oral scan image of the inside of the oral cavity.

In addition, the present invention is directed to providing a method and apparatus capable of quickly and accurately performing image registration between an oral scan image and a CT image by using an object of each tooth in an oral scan image and a CT image of the inside of the oral cavity.

The technical problems to be solved in the present invention are not limited to the technical problems mentioned above, and other technical problems not mentioned will be clearly understood by those of ordinary skill in the art from the following description.

A dental object detection method in an oral scan image according to an embodiment of the present invention for solving the above problems includes (1) extracting a region of interest comprising teeth from an oral scan image of a learning target, (2) generating a learning model by training from training data that form an object for each tooth in multiple directions of the extracted region of interest, and (3) detecting an object for multiple directions of each tooth in an oral scan image of a detection target using the learning model.

The dental object detection method in an oral scan image according to an embodiment of the present invention may further include extracting location, center point, and size information of each detected object.

The dental object detection method in an oral scan image according to an embodiment of the present invention may further include displaying each detected object on the oral scan image of the detection target.

The training data may include objects in two or more different directions (specific directions) for each tooth.

The specific direction may include a plane direction and an out-of-plane direction.

The dental object detection method in an oral scan image according to an embodiment of the present invention may further include forming a three-dimensional object including two or more objects for each detected tooth as a surface and displaying it on an oral scan image of a detection target.

The displaying may include displaying at least any one of location, center point, and size information of each detected object and each detected object together on the oral scan image of the detection target.

In addition, an image registration method using a dental object according to an embodiment of the present invention for solving the above problems includes (1) generating a plurality of reference points spaced apart from each other in an oral scan image of a registration target and a computed tomography (CT) image of a registration target, respectively, and (2) registering the oral scan image of the registration target and the CT image of the registration target by using the reference point of the oral scan image (a first reference point) and the reference point of the CT image (a second reference point).

The first and second reference points may include a reference point for one frontmost tooth in the front teeth area and a reference point for two teeth on both rearmost sides of the back teeth area.

The first reference point may be derived from an object which is a simplified shape of the teeth.

The generating may include (1) generating a learning model by training from training data that form an object for each tooth in multiple directions of the oral scan image of the learning target, (2) detecting an object for multiple directions of each tooth in the oral scan image of the registration target using the generated learning model, and (3) selecting a reference object from among the detected objects to generate a first reference point from the selected reference object.

The generating may include (1) generating a learning model by training with training data which form each object for n teeth (target tooth) (where n is a natural number equal to or greater than 3) spaced apart each other that are some teeth in multiple directions of the oral scan image of the learning target; (2) detecting an object for multiple directions of each target tooth in the oral scan image of the registration target using the generated learning model, and (3) selecting the detected object as a reference object to generate a first reference point from the selected reference object.

The reference object may include an object for one frontmost tooth of the front teeth area, and an object for two teeth on both rearmost sides of the back teeth area.

The generating may further include selecting a center point of the selected reference object as the first reference point.

An image registration apparatus according to an embodiment of the present invention includes (1) a storage for storing an oral scan image of a registration target and a computed tomography (CT) image of a registration target, and (2) a controllor for generating a plurality of reference points spaced apart from each other in the oral scan image and the CT image stored, respectively and then registering the oral scan image of the registration target and the CT image of the registration target by using the reference point of the oral scan image (a first reference point) and the reference point of the CT image (a second reference point).

The first and second reference points may include a reference point for one frontmost tooth in the front teeth area and a reference point for two teeth on both rearmost sides of the back teeth area.

The first reference point may be derived from an object which is a simplified shape of the teeth.

The controllor may detect an object for multiple directions of each tooth in the oral scan image of the registration target using a learning model generated by training from training data that form an object for each tooth in multiple directions of the oral scan image and the CT image of the learning target, and then select a reference object from among the detected objects to generate a first reference point from the selected reference object.

The controllor may detect an object for multiple directions of each target tooth in the oral scan image of the registration target using a learning model generated by training with training data which form each object for n teeth (target tooth) (where n is a natural number equal to or greater than 3) spaced apart each other that are some teeth in multiple directions of the oral scan image and the CT image of the learning target, and then select the detected object as a reference object to generate a first reference point from the selected reference object.

The present invention configured as described above can easily detect an object corresponding to each tooth in an oral scan image of the inside of the oral cavity, thereby improving the detection time and efficiency.

In addition, the present invention can provide extracted information such as location, center point, and size information of each detected object, and as a result, the extracted information can be utilized for operation such as use as a reference point of image registration with a CT image, identifying an implant placement position, and identifying a dental arch shape, etc., whereby the present invention has an advantage in that in addition to increasing usability, and the accuracy of the corresponding operation can be improved due to the high accuracy of the extracted information.

In addition, the present invention configured as described above has an advantage in that it can improve the speed and accuracy of the image registration by performing image registration between the oral scan image and the CT image using the object of each tooth that can be quickly and accurately extracted from the oral scan image and the CT image of the inside of the oral cavity.

BRIEF DESCRIPTION OF THE DRAWINGS

The above and other aspects, features, and advantages of the present invention will become more apparent to those of ordinary skill in the art by describing embodiments thereof in detail with reference to the accompanying drawings, in which.

DETAILED DESCRIPTION OF EXAMPLE EMBODIMENTS

The present invention and method of accomplishing the same may become more apparent through the following detailed description in relation to the accompanying drawings, and accordingly, those of ordinary skill in the art will be able to easily implement the technical idea of the present invention. In addition, in describing the present invention, when it is determined that a detailed description of a related known technology may unnecessarily obscure the subject matter of the present invention, the detailed description will be omitted.

The terms used in this specification are for the purpose of describing embodiments only and are not intended to be limiting to the present invention. In this specification, the singular form also includes the plural form in some cases, unless specifically specified in the phrase. In this specification, terms such as "include", "comprise", "provide" or "have" do not exclude the presence or addition of one or more other elements other than elements mentioned.

In this specification, terms such as "or" and "at least one" may represent one of the words listed together or a combination of two or more. For example, "A or B" and "at least one of A and B" may include only one of A or B, or may also include both A and B.

In this specification, descriptions according to "for example", etc. may not exactly match the information presented, such as the recited properties, variables, or values, and effects such as modifications, including tolerances, measurement errors, limits of measurement accuracy, and other commonly known factors should not limit the modes for carrying out the invention according to the various exemplary embodiments of the present invention.

In this specification, when an element is described as being "connected" or "linked" to another element, it will be understood that it may be directly connected or linked to the other element but intervening elements may also be present. On the other hand, when an element is referred to as being "directly connected" or "directly linked" to another element, it will be understood that there are no intervening elements present.

In this specification, when an element is described as being "on" or "adjacent to" another element, it will be understood that it may be directly "on" or "connected to" the other element but intervening elements may also be present. On the other hand, when an element is described as being "directly on" or "directly adjacent to" another element, it will be understood that there are no intervening elements present. Other expressions describing the relationship between the elements, for example, 'between' and 'directly between', and the like can be interpreted similarly.

In this specification, terms such as "first" and "second" may be used to describe various elements, but, the above elements should not be limited by the terms above. In addition, the above terms should not be construed as limiting the order of each component, and may be used for the purpose of distinguishing one element from another. For example, "first element" may be named as "second element" and similarly, "second element" may also be named as "first element."

Unless otherwise defined, all terms used in this specification may be used with meanings commonly understood by those of ordinary skill in the art. In addition, terms defined in a commonly used dictionary are not interpreted ideally or excessively unless explicitly and specifically defined.

Hereinafter, a preferred embodiment according to the present invention will be described in detail with reference to the accompanying drawings.

Figure 1:
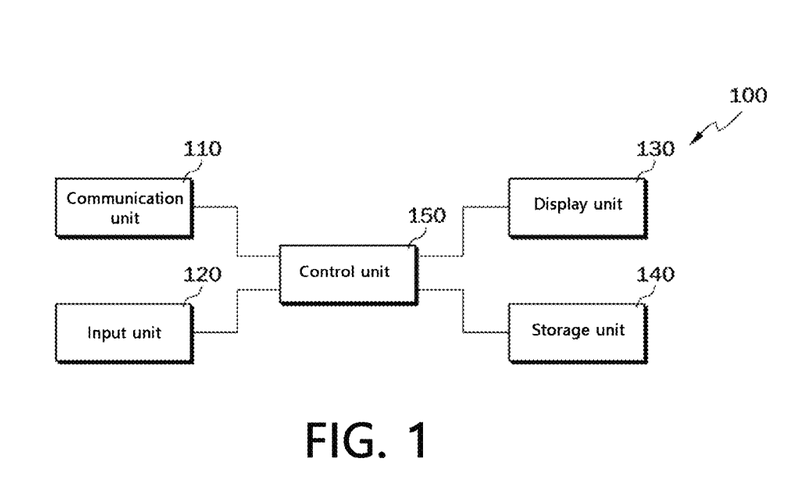
FIG. 1 is a block diagram of an image registration apparatus 100 according to an exemplary embodiment of the present invention.

FIG. 1 is a block diagram of an image registration apparatus 100 according to an exemplary embodiment of the present invention.

The image registration apparatus 100 according to an exemplary embodiment of the present invention is an electronic apparatus that performs image registration between an oral scan image and a CT image of the inside of the oral cavity.

The oral scan image is an image that provides information on the shape of the dental crown portion of the tooth exposed to the outside and the shape of the gum around the tooth. In this case, the oral scan image may be obtained by directly scanning the inside of the recipient's oral cavity through an oral scanner or may be obtained by scanning an impression model that mimics the inside of the recipient's oral cavity with an intaglio or a plaster model created through embossing of the impression model, and the scan image of the impression model can be inverted and used as an oral scan image.

The CT image is an image taken through a computed tomography (CT) device using radiation. That is, the CT image may represent information on the distribution of internal tissues such as the dental crown, dental root, and alveolar bone in the oral cavity and bone density information, etc., based on the transmittance of the radiation.

Referring to FIG. 1, an image registration apparatus 100 according to an embodiment may include a communicator 110, an input unit 120, a display 130, a storage 140, and a controller 150.

The communicator 110 is configured to communicate with an external device such as an image acquisition device (not shown) and a server (not shown), and may receive image data. For example, the communicator 110 may perform wireless communication such as 5th generation communication (5G), long term evolution-advanced (LTE-A), long term evolution (LTE), Bluetooth, Bluetooth low energy (BLE), and near field communication (NFC), and may perform wired communication such as cable communication.

In this case, the image data may include oral scan image data, CT image data, and the like.

The input unit 120 generates input data in response to a user's input. The input unit 120 includes at least one input means. For example, the input unit 120 may include a keyboard, a keypad, a dome switch, a touch panel, a touch key, a mouse, a menu button, and the like.

The display 130 displays display data according to the operation of the image registration apparatus 100. Such display data may include image data. For example, the display 130 may include a liquid crystal display (LCD), a light emitting diode (LED) display, an organic light emitting diode (OLED) display, a micro electro mechanical systems (MEMS) display, and an electronic paper display. In addition, the display 130 may be combined with the input unit 120 to be implemented as a touch screen, etc.

The storage 140 stores various information and programs necessary for the operation of the image registration apparatus 100. For example, the storage 140 may store image data received from an image acquisition device, etc., and an algorithm, etc. related to an image registration method using a dental object according to an embodiment of the present invention, which will be described later. Also, the storage 140 may store a learning model.

The controller 150 performs image registration between the oral scan image and the CT image received from an image acquisition device or server, etc. or pre-stored in the storage 140. To this end, the controller 150 may receive image data from the image acquisition device or server, etc. and store it in the storage 140. In addition, the controller 150 may control the operations of the communicator 110, the input unit 120, the display 130, and the storage 140.

Hereinafter, an image registration method using a dental object according to an embodiment of the present invention controlled by the controller 150 will be described.

Figure 2:
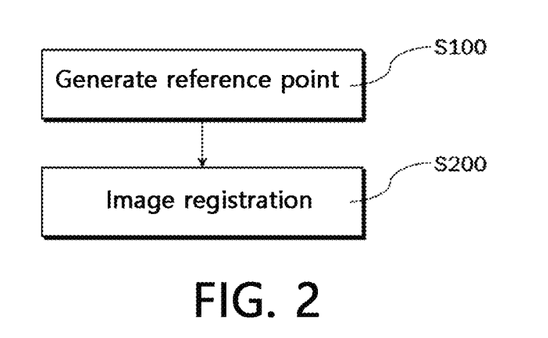
FIG. 2 a flowchart illustrating an image registration method using a dental object according to an exemplary embodiment of the present invention.

FIG. 2 a flowchart illustrating an image registration method using a dental object according to an exemplary embodiment of the present invention.

Referring to FIG. 2, the image registration method using a dental object according to an embodiment of the present invention may include S100 and S200 for performing image processing on image data.

First, in S100, the controllor 150 generates a plurality of reference points spaced apart from each other in an oral scan image and a CT image of a registration target, respectively. That is, the controllor 150 generates a reference point in the oral scan image of the registration target (hereinafter, referred to as a "first reference point"), and a reference point in the CT image of the registration target (hereinafter, referred to as a "second reference point").

Thereafter, in S200, the controllor 150 performs image registration by changing the registration target oral scan image or the registration target CT image using the first reference point and the second reference point so that the reference points coincide with each other.

In this case, the reference point is a point indicating a position with respect to a specific tooth (e.g., a position of a center point of the specific tooth), and is used during image registration. That is, in S200, the controllor 150 may perform image registration between the registration target oral scan image and the registration target CT image by changing the angle, size, position, etc. of these images, so that the specific first reference point and the specific second reference point corresponding thereto coincide with each other.

Figure 3:
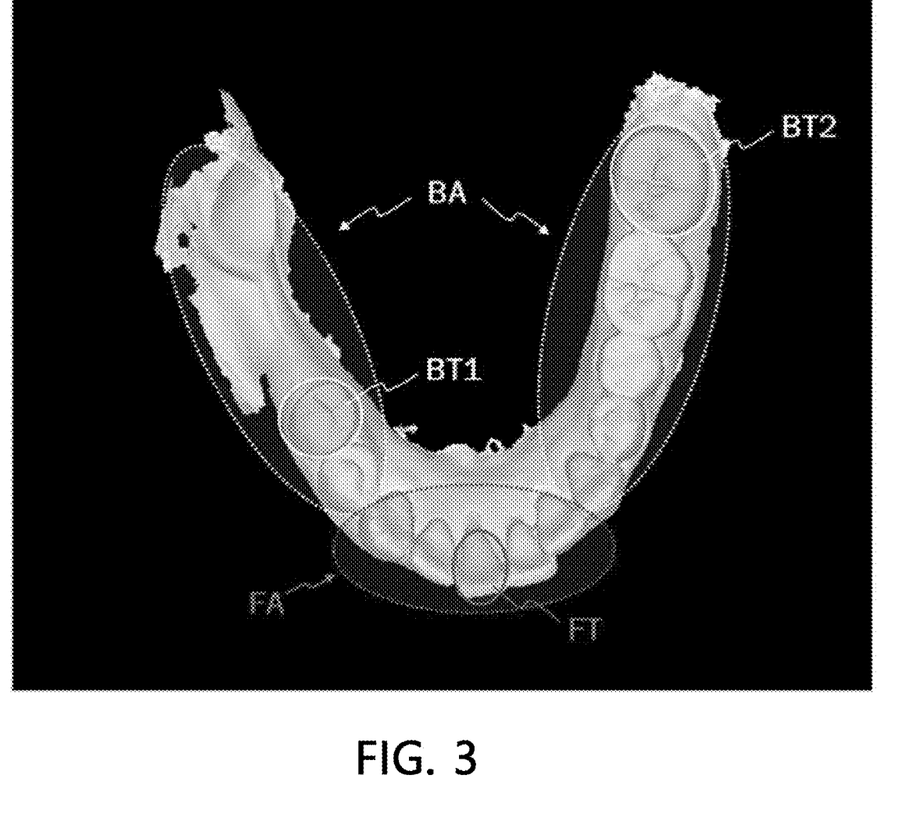
FIG. 3 shows a dental area comprising a front teeth area FA and a back teeth area BA.

FIG. 3 shows a dental area comprising a front teeth area FA and a back teeth area BA.

Referring to FIG. 3, the oral scan image and the CT image of the registration object include a dental area indicating the shape of the teeth. In this case, the dental area includes a front teeth area FA located in the front and a back teeth area BA located in the rear of the front teeth area FA. For example, the front teeth area FA may be an area in which teeth 1 to 3 are located, and the back teeth area BA may be an area in which teeth 4 to 8 are located.

In this case, the reference point may include a reference point for one frontmost tooth FT of the front teeth area FA (hereinafter, referred to as "frontmost reference point"), and a reference point for two teeth BT1 and BT2 on both rearmost sides of the back teeth area BA (hereinafter, referred to as "rearmost reference point"), respectively. That is, among the rearmost reference points, one is a reference point for one tooth selected among the teeth on the right side of the back teeth area (BA), and the other is a reference point for the other selected tooth among the teeth on the left side of the back teeth area (BA).

These frontmost and rearmost reference points are generated in each of the registration target oral scan image and the registration target CT image. As a result, in each image, one frontmost reference point and two rearmost reference points may form the vertexes of a triangle, providing a simpler and more accurate reference for changing the angle, size, position, etc. of the images during image registration between the registration target oral scan image and the registration target CT image.

In this case, the second reference point may be easily derived manually or through various algorithms from a three-dimensional coordinate information of the registration target CT image, which may even indicate information such as the structure, size, and position of the inside of the tooth. In this case, the derived second reference point may be a point indicating the position of the center point of the one frontmost tooth FT and the two rearmost teeth BT1 and BT2. Of course, the second reference point may be derived using a method of deriving (detecting) the first reference point, which will be described later. In this case, the description of the 'oral scan image' may be replaced with the description of the 'CT image'.

Meanwhile, it is necessary to derive the first reference point corresponding to the derived second reference point. However, since the first reference point should be derived from an oral scan image representing information on the surface of a tooth, when using a manual or conventional algorithm (using curvature information in an oral scan image), the accuracy of the first reference point is inevitably reduced.

Accordingly, the present invention derives the first reference point using an object OB which is a simplified shape of the teeth. This will be described in more detail according to S101 to S104 to be described later.

Figure 4:
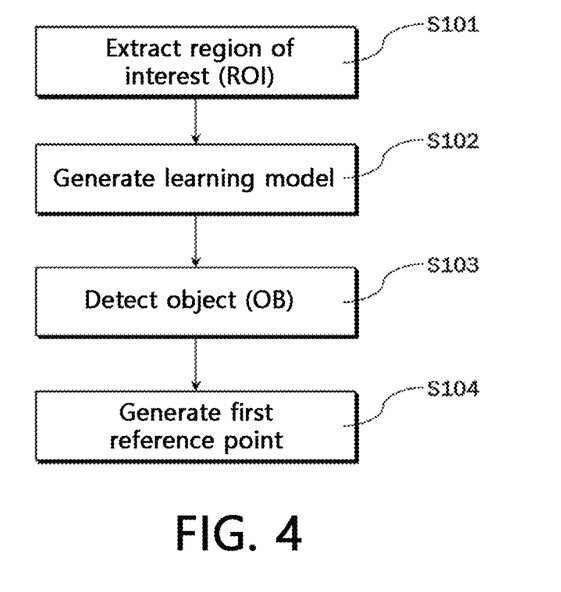
FIG. 4 is a more detailed flowchart of S100 of an image registration method using a dental object according to an exemplary embodiment of the present invention.
Figure 5:
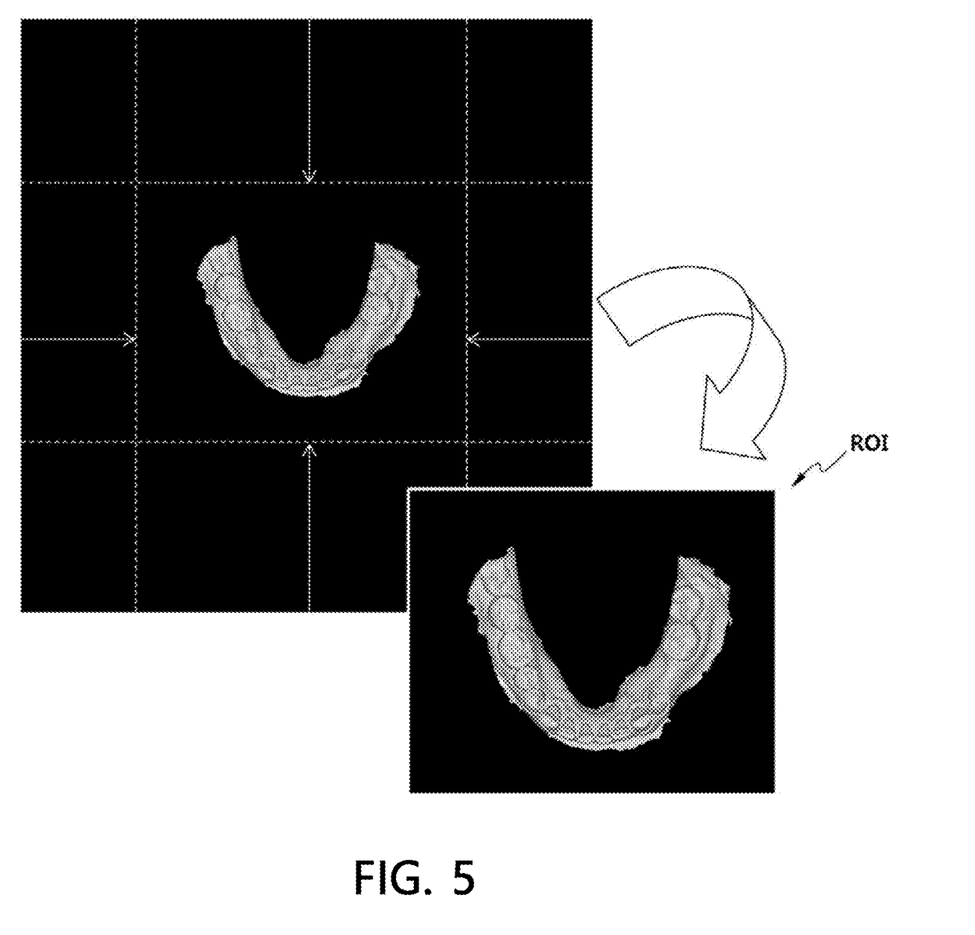
FIG. 5 is a diagram illustrating extraction from a region of interest ROI in a first learning target oral scan image.

FIG. 4 is a more detailed flowchart of S100 of an image registration method using a dental object according to an exemplary embodiment of the present invention, and FIG. 5 is a diagram illustrating extraction from a region of interest ROI in a first learning target oral scan image.

Referring to FIG. 5, in S101, the controllor 150 extracts a region of interest ROI including teeth from an oral scan image of the learning target (hereinafter, referred to as a "learning oral scan image"). That is, the learning oral scan image may include a dental area and an extra-dental area, and in S101, the controllor 150 may extract the dental area as a region of interest ROI.

Thereafter, in S102, the controllor 150 generates a learning model by training from training data that form an object OB1 for each tooth in multiple directions of the extracted region of interest ROI. In this case, the controllor 150 may train the prepared training data using a machine learning technique.

For example, machine learning technique is a supervised learning technique and may be one of techniques such as Artificial neural network, Boosting, Bayesian statistics, Decision tree, Gaussian process regression, Nearest neighbor algorithm, Support vector machine, Random forests, Symbolic machine learning, Ensembles of classifiers, Deep Learning.

That is, the training data may respectively include the learning oral scan image of the extracted region of interest ROI as an input value, and an object (OB) formed for each tooth in the corresponding image as a result value (target value) forming a set for the corresponding input value. In this case, the object OB1 is one that is set in various directions in the region of interest ROI of the learning oral scan image, and may have a variety of shapes that simplify the shape of the corresponding tooth in the corresponding direction to correspond to the shape of each tooth (a shape that covers the area of the corresponding tooth in the corresponding direction, but is simpler than the shape of the tooth), that is, a shape such as a circle or a polygon. In addition, the result value of the training data for the object OB1 may include position information, center point information, and size information occupied by the object OB1 in the region of interest ROI.

In addition, the learning model is a model trained through supervised learning by a machine learning technique using training data, and includes a rule function for matching the input value and the result value.

Figure 6:
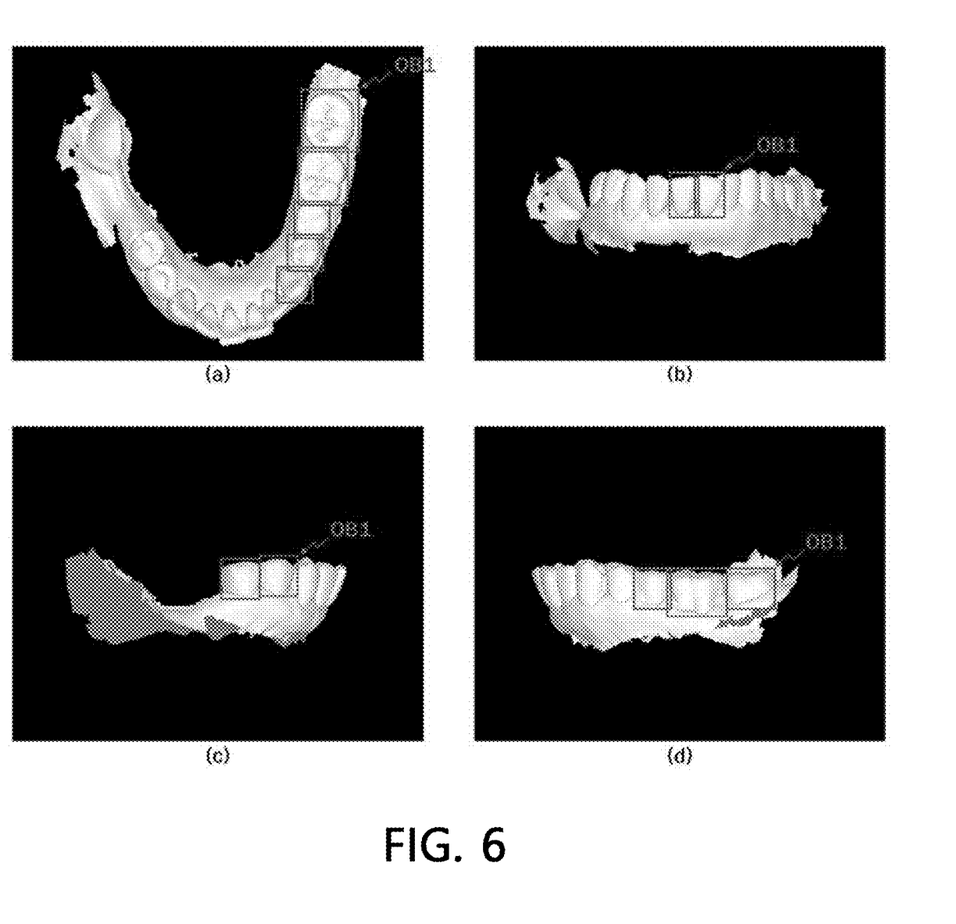
FIG. 6 shows a state in which an object is set for four directions in a region of interest ROI of a second learning target oral scan image.

FIG. 6 shows a state in which an object OB1 is set for four directions in a region of interest ROI of a learning target oral scan image. That is, FIG. 6(a) shows a plane direction, FIG. 6(b) shows a front direction, FIG. 6(c) shows a left direction, and FIG. 6(d) shows a right direction, respectively.

For example, as shown in FIG. 6, in the region of interest ROI of the learning oral scan image, the object OB1 for four directions, i.e., plane, front, left, and right directions, may be set. In this case, the setting of the object OB1 may be set by a user through the input unit 120. As a result, the training data may include the object OB1 in at least two directions (specific directions) for each tooth. In this case, the specific direction may include a plane direction and an out-of-plane direction (a front direction, a left direction, or a right direction).

That is, the object OB1 may be formed in the plane direction and the front direction, respectively, of the region of interest ROI for teeth 1 to 3 seen in the front direction of the region of interest ROI. In addition, the object OB1 may be formed in the left direction and the front direction, respectively, of the region of interest ROI for teeth 4 to 8 seen in the left direction of the region of interest ROI. In addition, the object OB1 may be formed in the right direction and the front direction, respectively, of the region of interest ROI for teeth 4 to 8 seen in the right direction of the region of interest ROI. In addition, as described above, the object OB1 for all teeth may be formed in the plane direction of the region of interest ROI.

The object OB1 in the plane direction is a shape obtained by simplifying the shape of the corresponding tooth in the plane direction, and the object OB1 in the out-of-plane direction is a shape obtained by simplifying the shape in the out-of-plane direction of the corresponding tooth. Accordingly, the object OB1 in the plane direction may act as a medium providing information about the plane of the corresponding tooth, and the object OB1 in the out-of-plane direction may act as a medium providing information about one side (height, etc.) of the corresponding tooth.

For example, the object OB1 in the plane direction with respect to the teeth of the mandible may act as a medium providing information about the upper surface of the corresponding tooth, and the object OB1 in the out-of-plane direction with respect to the teeth of the mandible may act as a medium providing information about one side of the corresponding tooth. Similarly, the object OB1 in the plane direction with respect to the teeth of the maxilla may act as a medium providing information about the lower surface of the corresponding tooth, and the object OB1 in the out-of-plane direction with respect to the teeth of the maxilla may act as a medium providing information about one side of the corresponding tooth.

Thereafter, in S103, the controllor 150 detects an object OB2 for multiple directions of each tooth in the oral scan image of the registration target using the learning model generated in S102. That is, the controllor 150 may input the registration target oral scan image to the learning model as an input value, and as a result, the learning model may output the object OB2 for the corresponding registration target oral scan image as a result value.

Figure 7:
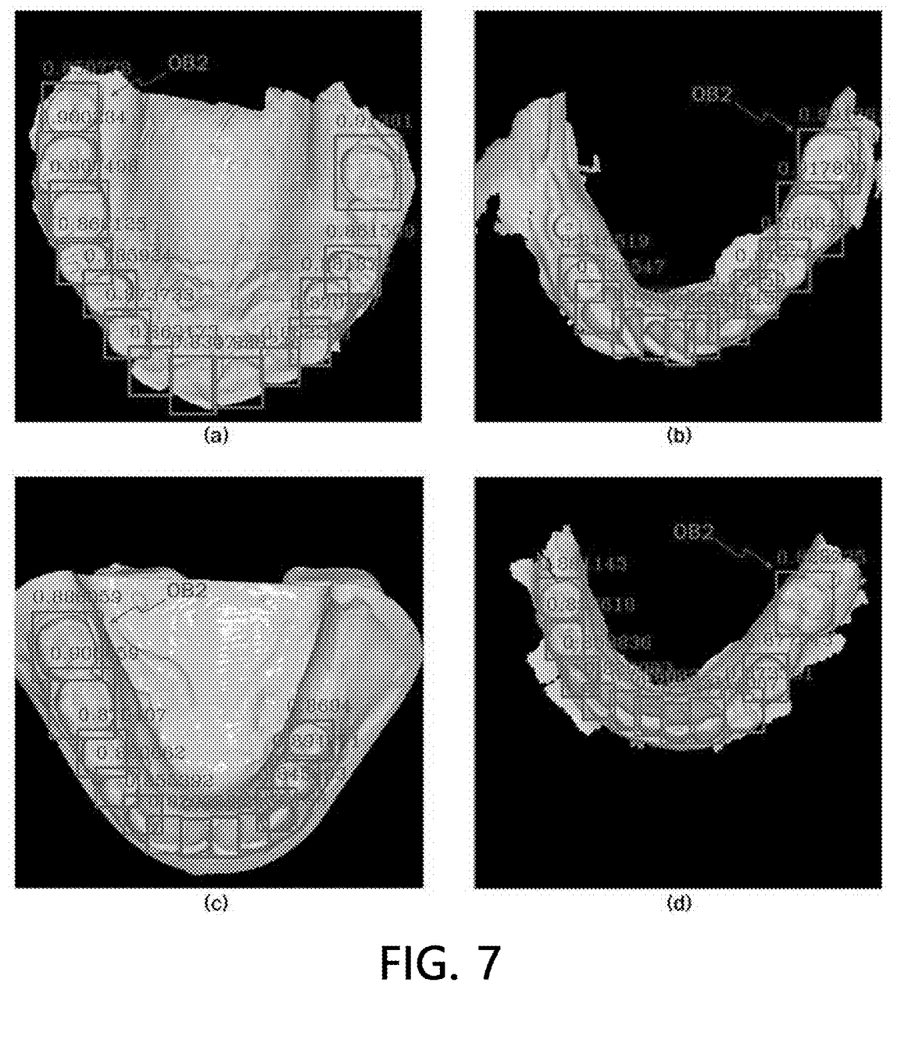
FIG. 7 is a diagram illustrating an object detected in oral scan images of a first to fourth registration targets.
Figure 8:
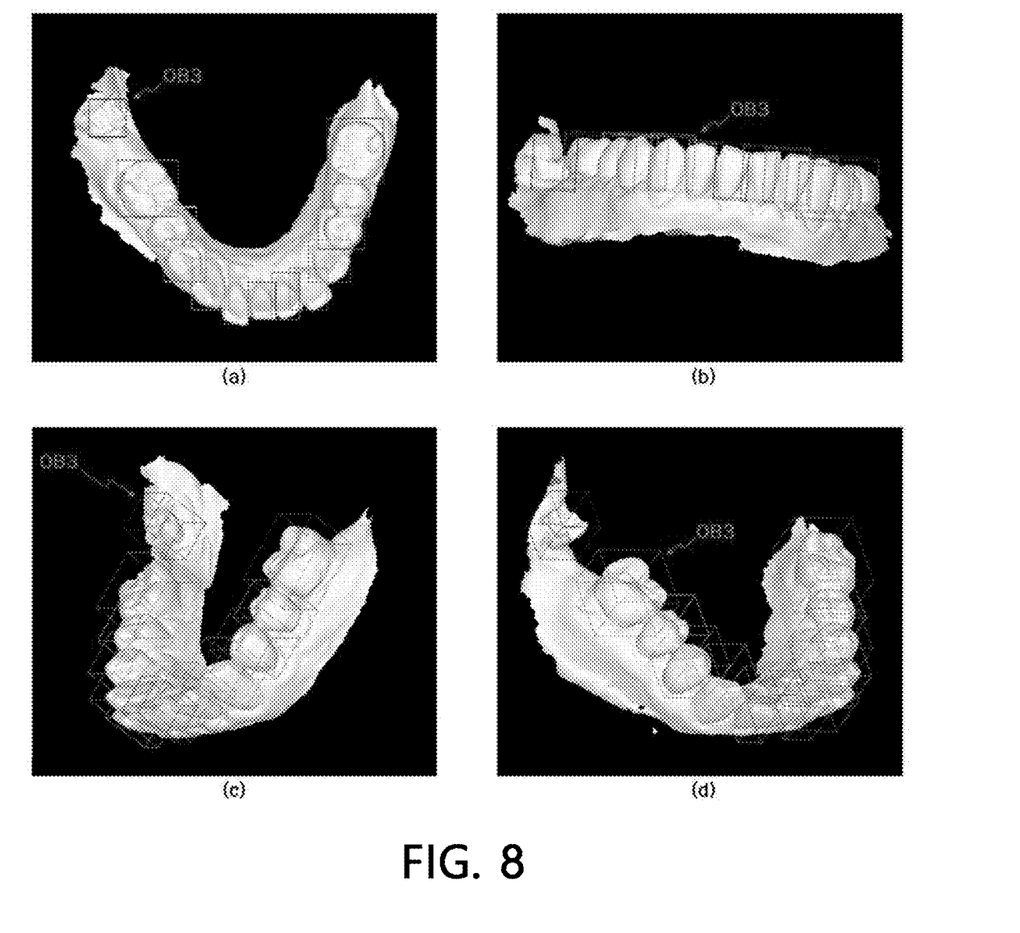
FIG. 8 is a diagram illustrating a three-dimensional object detected in various directions in an oral scan image of a fifth registration target.

FIG. 7 is a diagram illustrating the object OB2 detected in oral scan images of a first to fourth detection targets, and FIG. 8 is a diagram illustrating a three-dimensional object OB3 detected in various directions in an oral scan image of a fifth detection target.

Referring to FIG. 7, the learning model may output (detect) the object OB2 corresponding to multiple directions in S102 from the registration target oral scan image.

That is, for teeth 1 to 3 seen in the front direction of the registration target oral scan image, the corresponding object OB2 may be detected in the plane direction and the front direction of the registration target oral scan image, respectively. In addition, for teeth 4 to 8 seen in the left direction of the registration target oral scan image, the corresponding object OB2 may be detected in the left direction and the front direction of the registration target oral scan image, respectively. In addition, for teeth 4 to 8 seen in the right direction of the registration target oral scan image, the corresponding object OB1 may be detected in the right direction and the front direction of the registration target oral scan image, respectively. In addition, as described above, the object OB2 for all teeth may be detected in the plane direction of the region of interest ROI.

Meanwhile, in S103, the controllor 150 may generate (detect) a three-dimensional object OB3 by using two or more objects OB2 for each detected tooth. That is, the controllor 150 may generate a three-dimensional shape including two or more objects OB2 for each detected tooth as a surface, and detect the three-dimensional shape as the three-dimensional object OB3.

In this case, the object OB2 generated by the learning model may have a variety of shapes that simplify the shape of the corresponding tooth in the corresponding direction to correspond to the shape of each tooth (a shape that covers the area of the corresponding tooth in the corresponding direction, but is simpler than the shape of the tooth), that is, a shape such as a circle or a polygon. In addition, the three-dimensional object OB3 may have various three-dimensional shapes that simplify the three-dimensional shape of the corresponding tooth to correspond to the three-dimensional shape of each tooth (a shape that covers the volume of the corresponding tooth, but is simpler than the three-dimensional shape of the tooth), that is, a shape such as a cylinder, an elliptical cylinder, a polyprism, a truncated cone, or a polygonal truncated pyramid.

For example, as shown in FIG. 8, when the three-dimensional object OB3 is a rectangular parallelepiped, the controllor 150 may detect a three-dimensional object OB3 having a rectangular parallelepiped shape with respect to the corresponding tooth by generating a rectangular parallelepiped having two objects OB2 for a certain tooth as a first surface and a second surface, and having virtual surfaces perpendicular to the first and second surfaces as the remaining surfaces.

That is, the object OB2 in the plane direction represents the shape of the corresponding tooth in the plane direction, and the object OB2 in the out-of-plane direction represents the shape in the out-of-plane direction of the corresponding tooth. Accordingly, the object OB2 in the plane direction may act as a medium providing information about the plane of the corresponding tooth, and the object OB2 in the out-of-plane direction may act as a medium providing information about one side (height, etc.) of the corresponding tooth.

As a result, the controllor 150 may detect a three-dimensional object OB3 having an object OB2 in the plane direction as an upper surface or a lower surface of the corresponding tooth and an object OB2 in the out-of-plane direction as one side of the corresponding tooth. In this case, the controllor 150 may add surfaces other than the surface formed by the object OB2 in the plane direction and the object OB2 in the out-of-plane direction as virtual surfaces. That is, the controllor 150 may add one or more virtual surfaces perpendicular to the object OB2 in the plane direction as the other one side, and add a virtual surface parallel to the object OB2 in the plane direction as another plane (a lower surface when the corresponding tooth is included in the mandible, and an upper surface when the corresponding tooth is included in the maxilla).

Thereafter, in S103, the controllor 150 may extract location information (location coordinates in the oral scan image), center point information (center point coordinates in the oral scan image), and size information of each detected object OB2 and OB3. In this case, the location information, center point information, and size information of the object OB2 may be output together with the object OB2 as a result value for the input value of the learning model.

However, the controller 150 may extract location information, center point information, and size information of the corresponding three-dimensional object OB3 by using location information, center point information, and size information for two or more related objects OB2 used to generate each three-dimensional object OB3.

For example, as shown in FIG. 8, when the three-dimensional object OB3 is a rectangular parallelepiped, the controllor 150 may extract location information, center point information, and size information of the corresponding three-dimensional object OB3 by using location information, center point information, and size information of the objects OB2 constituting the first and second surfaces of the rectangular parallelepiped.

Thereafter, the controllor 150 may display each detected object OB2 and OB3 on the registration target oral scan image. That is, the controllor 150 may display the respective objects OB2 and OB3 on the registration target oral scan image by using the location information, center point information, and size information of each detected object OB2 and OB3. However, in order to make the distinction for each tooth more clear, as shown in FIG. 6, the controller 150 may display the detected objects OB2 and OB3 in a different color for each tooth on the registration target oral scan image.

In this case, the controllor 150 may display at least any one of location information, center point information, and size information of each detected object OB2 and OB3 and each detected object OB2 and OB3 together on the registration target oral scan image.

Meanwhile, although FIGS. 5 to 8 show only the teeth of the mandible, the present invention is not limited thereto, and the object detection operation according to the present invention may be equally applied to the teeth of the maxilla.

Figure 9:
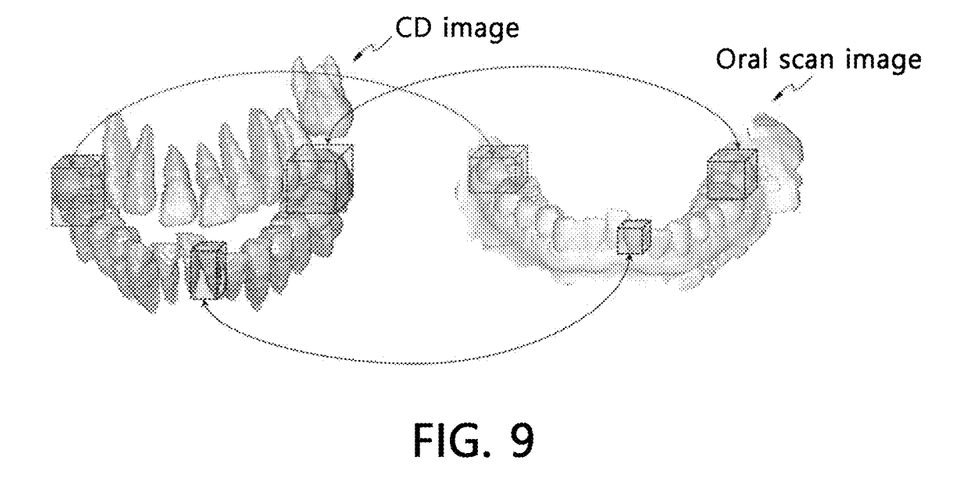
FIGS. 9 and 10 show an image registration process between an oral scan image and a CT image of a registration target.
Figure 10:
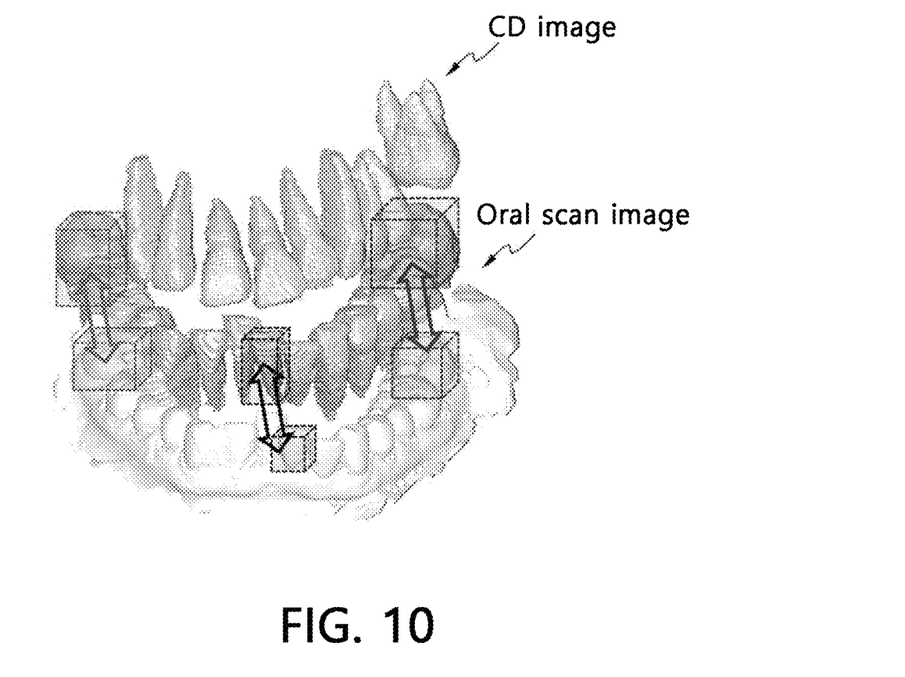
Figure 11:
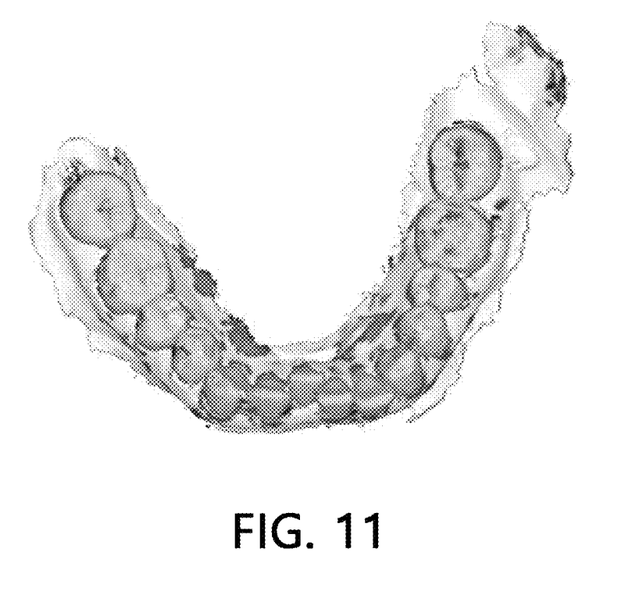
FIG. 11 shows a state after image registration between an oral scan image and a CT image of a registration target.

FIGS. 9 and 10 show an image registration process between an oral scan image and a CT image of a registration target. In this case, in FIGS. 9 and 10, the dotted rectangular parallelepiped indicates the regions of the frontmost tooth FT and the rearmost tooth BT1 and BT2 in each image. That is, FIGS. 9 and 10 show a process of image registration so that the first reference point and the second reference point in each image are matched with each other. In addition, FIG. 11 shows a state after image registration between an oral scan image and a CT image of a registration target.

Thereafter, in S104, the controllor 150 selects a reference object from among the detected objects OB2 and OB3 to generate a first reference point from the selected reference object. In this case, the reference object may include an object for one frontmost tooth FT of the front teeth area FA (hereinafter, referred to as "frontmost object"), and an object for two teeth BT1 and BT2 on both rearmost sides of the back teeth area BA (hereinafter, referred to as "rearmost object"). In addition, the controllor 150 may select a center point (a center point of a surface or a volume) of the reference object as the first reference point.

The present invention can easily detect the objects OB2 and OB3 corresponding to each tooth in the oral scan image of the inside of the oral cavity, thereby improving the detection time and efficiency.

In addition, the present invention can provide extracted information such as location, center point, and size information of each detected object (OB2, OB3), and as a result, the extracted information can be utilized as a reference point for image registration with the CT image, and the accuracy of image registration can be improved due to the high accuracy of the extracted information.

That is, referring to FIGS. 9 and 10, during image registration with a CT image, center point information, etc. on a plurality of objects OB2 and OB3 that can be quickly extracted can be used as a first reference point for image registration, and such information on the first reference point is more accurate than the information according to the conventional tooth detection method using the curvature information, and so, as a result, as shown in FIG. 11, the speed and accuracy of image registration can be improved accordingly.

Meanwhile, in S100, the controllor 150 may control the learning model to output the frontmost object and the rearmost object as output values thereof.

In this case, in S102, the controller 150 generates a learning model by training according to a machine learning technique with the training data which form each object OB1 for n teeth (hereinafter referred to as "target tooth") (where n is a natural number equal to or greater than 3) spaced apart each other that are some teeth in multiple directions of the extracted region of interest ROI. That is, the target tooth includes a frontmost tooth FT and a rearmost tooth BT. Accordingly, the learning model is trained using the training data that form the object OB1 corresponding to the frontmost object and the rearmost object. In addition, in S103, the controllor 150 detects an object OB2 for multiple directions of each target tooth in the oral scan image of the registration target using the learning model generated in S102. In addition, it detects a three-dimensional object OB3 using this object OB2. As a result, in S104, the controllor 150 selects the detected objects OB2 and OB3 as a reference object to generate a first reference point from the selected reference object. Other than that, it is the same as the contents of S101 to S104 described above.

In the detailed description of the present invention, although specific embodiments have been described, it is apparent that various modifications are possible without departing from the scope of the present invention. Therefore, the scope of the present invention is not limited to the described embodiments, and should be defined by the following claims and their equivalents.

A dental object detection method, and image registration method and apparatus using a dental object according to the present invention may be used in various dental treatment fields such as implant operation.

What is claimed is:

1. An image registration method using a dental object, the method comprising:
   generating a plurality of reference points spaced apart from each other in an oral scan image of a registration target and a computed tomography (CT) image of a registration target, respectively; and
   registering the oral scan image of the registration target and the CT image of the registration target by using the reference point of the oral scan image (a first reference point) and the reference point of the CT image (a second reference point),
   wherein the first and second reference points comprise a reference point for one frontmost tooth in the front teeth area and a reference point for two teeth on both rearmost sides of the back teeth area, and wherein the first reference point is derived from an object which is a simplified shape of the teeth.

2. The method of claim 1, wherein the generating the reference point comprises:
generating a learning model by training from training data that form an object for each tooth in multiple directions of the oral scan image of the learning target;
detecting an object for multiple directions of each tooth in the oral scan image of the registration target using the generated learning model; and
selecting a reference object from among the detected objects to generate a first reference point from the selected reference object.

3. The method of claim 1, wherein the generating the reference point comprises:
generating a learning model by training with training data which form each object for n teeth (target tooth) (where n is a natural number equal to or greater than 3) spaced apart each other that are some teeth in multiple directions of the oral scan image of the learning target;
detecting an object for multiple directions of each target tooth in the oral scan image of the registration target using the generated learning model; and
selecting the detected object as a reference object to generate a first reference point from the selected reference object.

4. The method of claim 3, wherein the reference object comprises an object for one frontmost tooth of the front teeth area, and an object for two teeth on both rearmost sides of the back teeth area.

5. The method of claim 3, wherein the generating the reference point further comprises selecting a center point of the selected reference object as the first reference point.

6. An image registration apparatus comprising:
a storage for storing an oral scan image of a registration target and a computed tomography (CT) image of a registration target; and
a controllor for generating a plurality of reference points spaced apart from each other in the oral scan image and the CT image stored, respectively and then registering the oral scan image of the registration target and the CT image of the registration target by using the reference point of the oral scan image (a first reference point) and the reference point of the CT image (a second reference point),
wherein the first and second reference points comprise a reference point for one frontmost tooth in the front teeth area and a reference point for two teeth on both rearmost sides of the back teeth area, and
wherein the first reference point is derived from an object which is a simplified shape of the teeth.

7. The apparatus of claim 6, wherein the controllor:
detects an object for multiple directions of each tooth in the oral scan image of the registration target using a learning model generated by training from training data that form an object for each tooth in multiple directions of the oral scan image and the CT image of the learning target, and then
selects a reference object from among the detected objects to generate a first reference point from the selected reference object.

8. The apparatus of claim 6, wherein the controllor:
detects an object for multiple directions of each target tooth in the oral scan image of the registration target using a learning model generated by training with training data which form each object for n teeth (target tooth) (where n is a natural number equal to or greater than 3) spaced apart each other that are some teeth in multiple directions of the oral scan image and the CT image of the learning target; and then
selects the detected object as a reference object to generate a first reference point from the selected reference object.

* * * * *